(12) United States Patent
Pompa

(10) Patent No.: US 10,179,333 B2
(45) Date of Patent: Jan. 15, 2019

(54) INTEGRAL CAP SAMPLE CUP

(71) Applicant: Premier Lab Supply Inc., Port St. Lucie, FL (US)

(72) Inventor: Donato Pompa, Port St Lucie, FL (US)

( * ) Notice: Subject to any disclaimer, the term of this patent is extended or adjusted under 35 U.S.C. 154(b) by 0 days.

(21) Appl. No.: 14/862,546

(22) Filed: Sep. 23, 2015

(65) Prior Publication Data

US 2017/0080415 A1 Mar. 23, 2017

(51) Int. Cl.
*B01L 3/00* (2006.01)
*G01N 21/77* (2006.01)
*G01N 23/223* (2006.01)

(52) U.S. Cl.
CPC ............ *B01L 3/502* (2013.01); *G01N 23/223* (2013.01); *B01L 2200/0621* (2013.01); *B01L 2200/141* (2013.01); *B01L 2300/042* (2013.01); *B01L 2300/043* (2013.01); *B01L 2300/044* (2013.01); *B01L 2300/047* (2013.01); *B01L 2300/048* (2013.01); *B01L 2300/0832* (2013.01); *B01L 2300/0848* (2013.01); *B01L 2300/0861* (2013.01); *G01N 2223/307* (2013.01)

(58) Field of Classification Search
CPC ................................. B01L 3/502; G01N 21/27
USPC .......................................................... 422/557
See application file for complete search history.

(56) References Cited

U.S. PATENT DOCUMENTS

| | | | |
|---|---|---|---|
| 7,729,471 B2* | 6/2010 | Burdett, Jr. ........ | G01N 23/2204 378/204 |
| 2004/0050850 A1* | 3/2004 | Richter .............. | B65D 77/0466 220/495.06 |
| 2005/0032239 A1* | 2/2005 | Katz .................... | A61B 10/007 436/177 |
| 2006/0011532 A1* | 1/2006 | Van Davelaar .... | G01N 30/6091 210/198.2 |
| 2009/0209882 A1* | 8/2009 | Saunders ............ | B01L 3/50825 600/573 |
| 2011/0051134 A1* | 3/2011 | Solazzi ................... | B01L 3/508 356/300 |
| 2014/0242685 A1* | 8/2014 | Knoppke ................ | B01L 3/502 435/289.1 |

* cited by examiner

*Primary Examiner* — Jill A Warden
*Assistant Examiner* — Jacqueline Brazin
(74) *Attorney, Agent, or Firm* — Joseph Beckman

(57) ABSTRACT

This invention relates to the design and construction of a novel sample cup including an integral cap for use in XRF Spectroscopy.

22 Claims, 6 Drawing Sheets

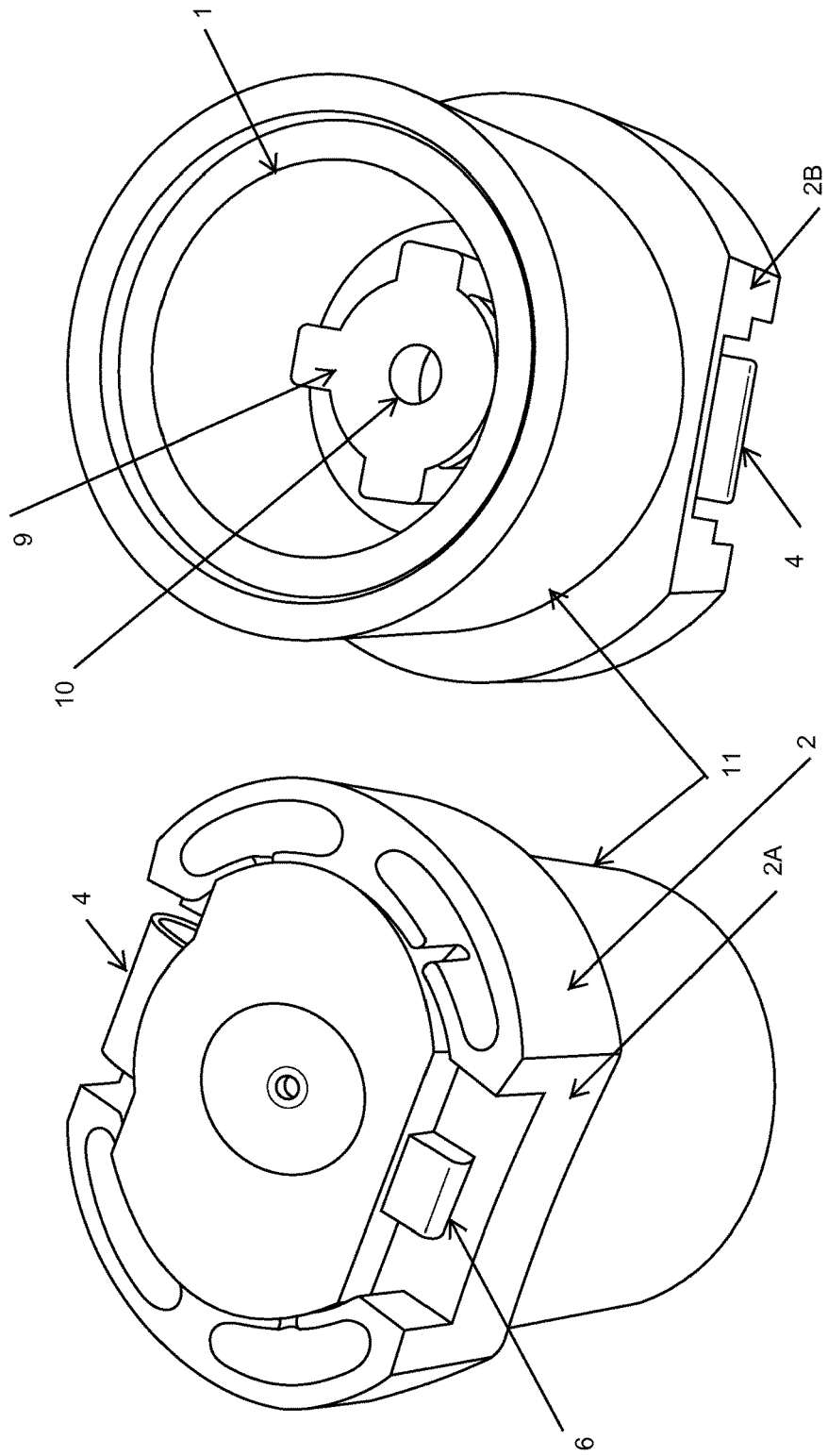

INTEGRAL CAP SAMPLE CUP

FIELD OF THE INVENTION

This invention relates to the design and construction of a novel sample cup including an integral cap for use in XRF Spectroscopy.

BACKGROUND OF THE INVENTION

The present invention describes a novel sample cup including an integral cap for use in XRF Spectroscopy.

Spectroscopic analysis (XRF Spectroscopy) utilizes sample cups to contain liquid or powder samples for elemental analysis. Sample cups generally have a thin transparent film bottom and may include a top end formed integral with the cup body known as a single ended design. Alternatively, the sample cup may include a second thin film or be secured at the top end, known as a double open end design. Sample cups are generally delivered to the analyst in parts comprised of a side wall member and complementary secondary member, which members are assembled in combination with a separate thin film component to construct a single sample cup. The sample cup, with its liquid or powder sample contained therein, is then manually transported to an XRF instrument and placed in a holder, thin film bottom down, for analysis.

Sample cups are configured in various sizes to accommodate different analytical instruments and testing purposes. Some sample cups are dimensioned very small and are particularly difficult to handle. A sample cup design utilizing a separate cap assembly to be manually applied to the sample cup body after deposit of the sample into the sample cup body requires manipulating the sample cup body, sample deposit and cap assembly. This creates handling problems and opportunities for contamination of the sample and contamination or damage to the thin film assembled to the bottom of the sample cup. The ability to reduce the number of manipulated items, particularly when sized very small, increases technician productivity and reduces the opportunities for contamination or damage to the sample cup and sample specimen.

The present invention avoids these disadvantages, being easily manipulated with one hand while dispensing a liquid sample and then being securely sealed for safe and contaminant-free handling.

BRIEF DESCRIPTION OF THE DRAWINGS

FIGS. 1-9 are various views (elevation and perspective) of two embodiments of the integral cap sample cup.

DETAILED DESCRIPTION OF THE INVENTION

Figure 1:
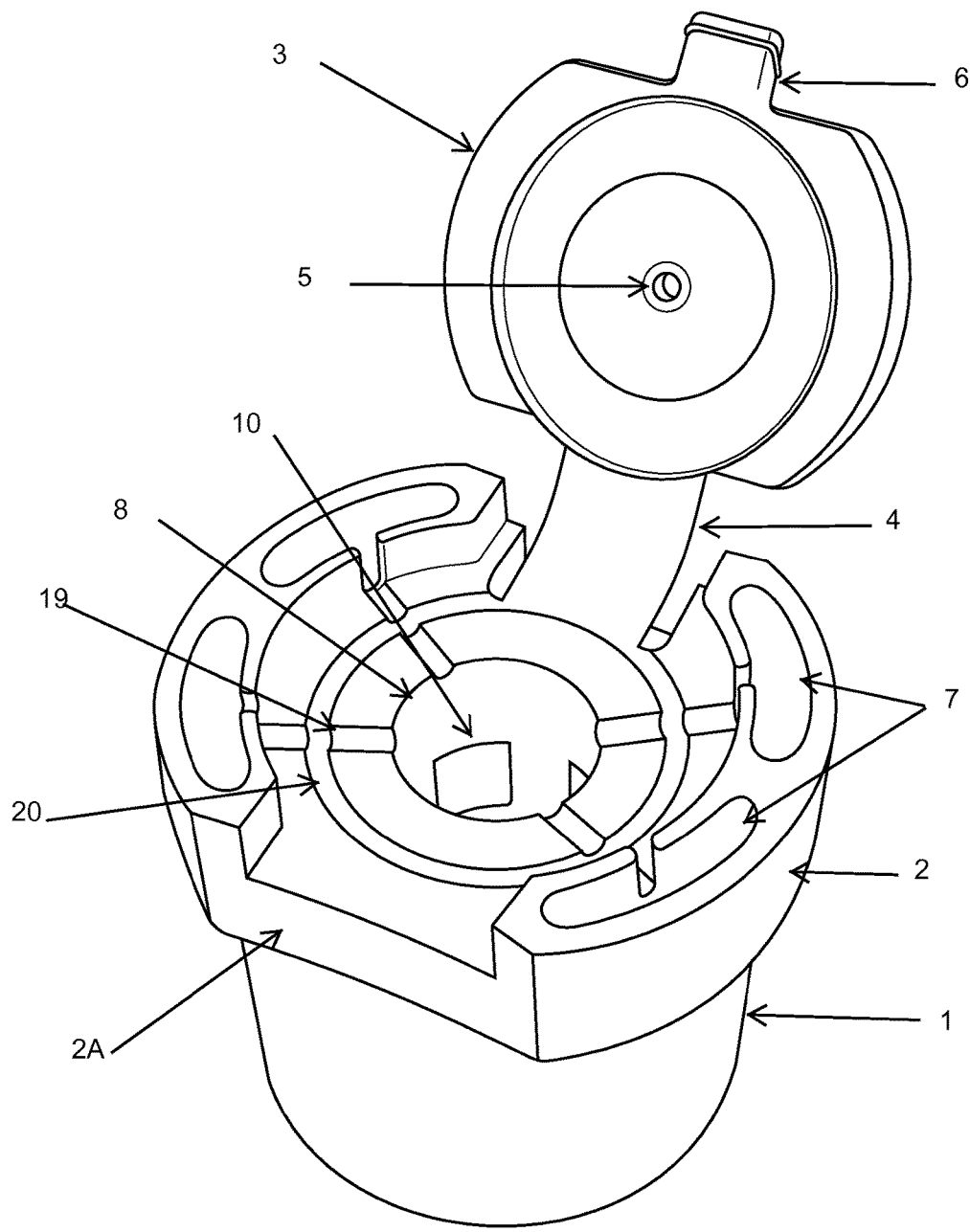

Shown in FIG. 1 is an integral cap sample cup comprising a sample cup lower body (1) with a bottom open end, a flanged cup upper body (2) with a top open end, integral cap (3) secured to upper body (2) via a hinge (4). The cap (3) includes a vent hole (5) for pressure equalization and gas release, particularly when volatile liquid samples exist, and also includes a pull tab (6) for manipulation of the cap (3) and securing said cap in a closed position on upper body (2). Upper body (2) includes overflow chambers (7) for the collection of escaping liquids or collection of liquefied escaping gases during testing. Channels to funnel any escaping liquids or gases to said overflow chambers are provided as indicated. A first channel (19) extends from the top outside edge of an inner chamber (8) to an overflow chamber (7). A second channel (20) is situated circumferentially about the upper body top open end. The second channel may completely or partially encircle the upper body top open end. Suspended from upper body (2) is inner chamber (8). Inner chamber (8) includes one or more cutouts (10) to allow pipette deposited liquid to settle within the lower body (1) interior and be contained by a thin film secured by an outer member (not shown in FIG. 1). Said inner chamber is dimensioned to allow for insertion of a pipette and contains a bottom stop (not shown in FIG. 1) to prevent said pipette from contacting and damaging the thin film. The upper body may be dimensioned to include parallel opposing flat surfaces (2A and 2B) disposed perpendicular to said top open end of said upper body (2).

Shown in FIG. 2 is a partial top perspective view of the integral cap sample cup with the integral cap in the closed position. Said cap may be secured in the closed position via frictional fit with upper body (2) or via a hook and slot configuration.

Shown in FIG. 3 is a partial bottom perspective view of the integral cap sample cup with the integral cap in the closed position. In this view, the bottom stop (9) of the inner chamber (8) is shown with a cutout (10) for deposit of the liquid into the lower body interior. The outer member (11) is shown in place over lower body (1). In assembly, a thin film is placed over the bottom open end of lower body (1) and said outer member (11) then secures said thin film by friction placement as shown.

Figure 4:
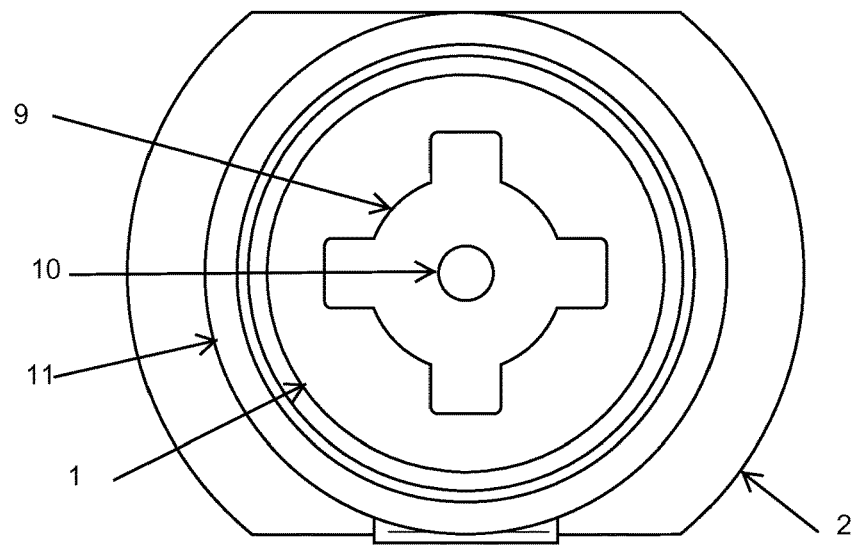

Shown in FIG. 4 is a bottom elevation view of the integral cap sample cup. The lower body (1), outer member (11) and upper body (2) are shown along with the bottom stop (9) of inner chamber (8) and bottom cutout (10).

Figure 5:
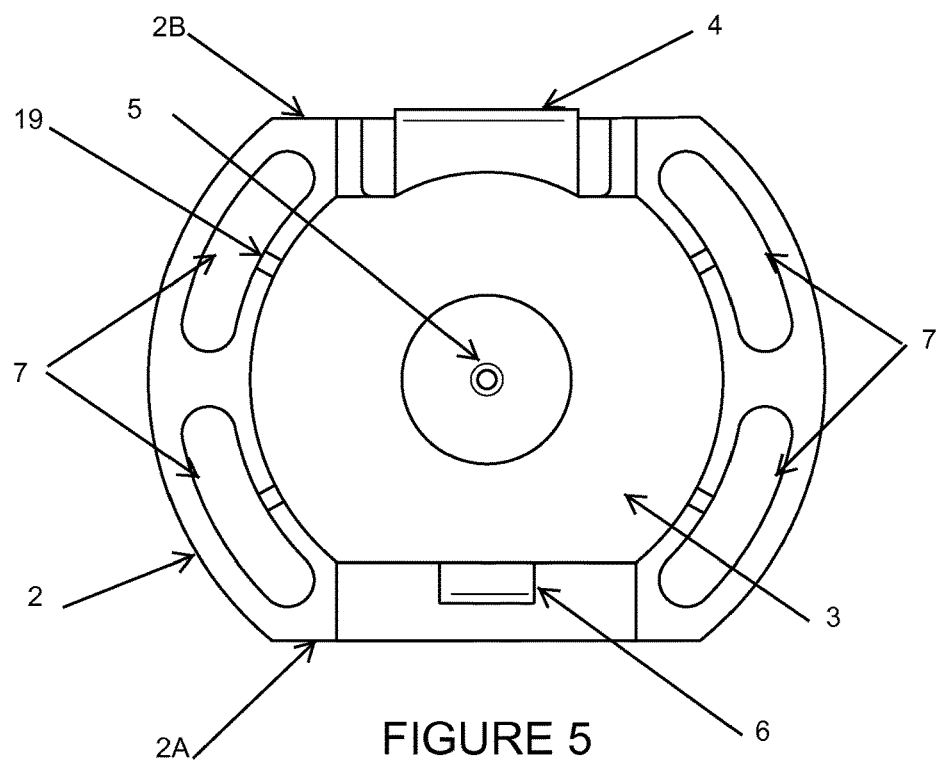

Shown in FIG. 5 is a top elevation view of the integral cap sample cup. The upper body (2) is shown along with the cap (3) in a closed position, hinge (4) and pull tab (6). Four overflow chambers (7) are evident along with vent hole (5).

Figure 6:
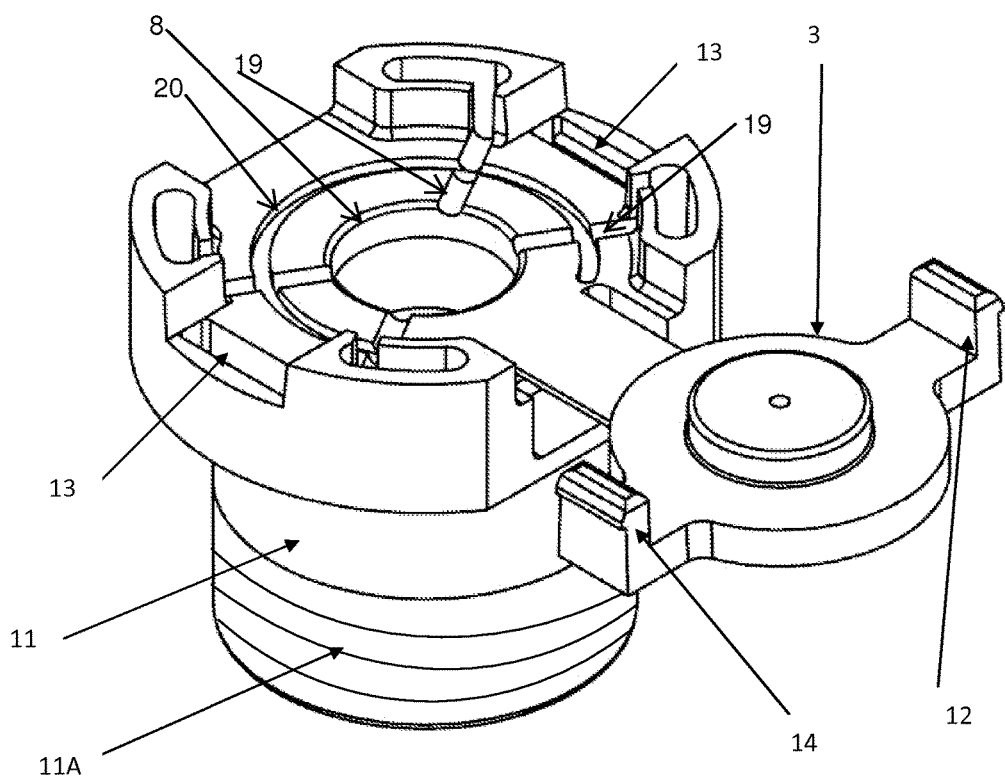

Shown in FIG. 6 is the integral cap sample cup with an alternative cap. The cap utilizes two opposing locking tabs (12). Upon closing said cap, each locking tab inserts in a corresponding slot (13) located on the upper surface of the upper body. Said locking tabs may secure the cap via a frictional fit with their corresponding slots. Alternatively, each locking tab may utilize a hooked portion (14) which mates with a corresponding hooked portion (15) positioned within each of said corresponding slots. In lieu of hooked portions, the locking tab and corresponding slot may utilize a groove and detent method to secure the cap in a closed position. First channel (19) and second channel (20) are shown in relation to inner chamber (8) and upper body (2) top open end. Also shown in FIG. 6 is outer member (11) configured to include a gripping means (11A) situated on a lower portion of said outer member to facilitate handling of the assembled sample cup. The gripping means may be ridges, stippling or any raised or embedded pattern.

Figure 7:
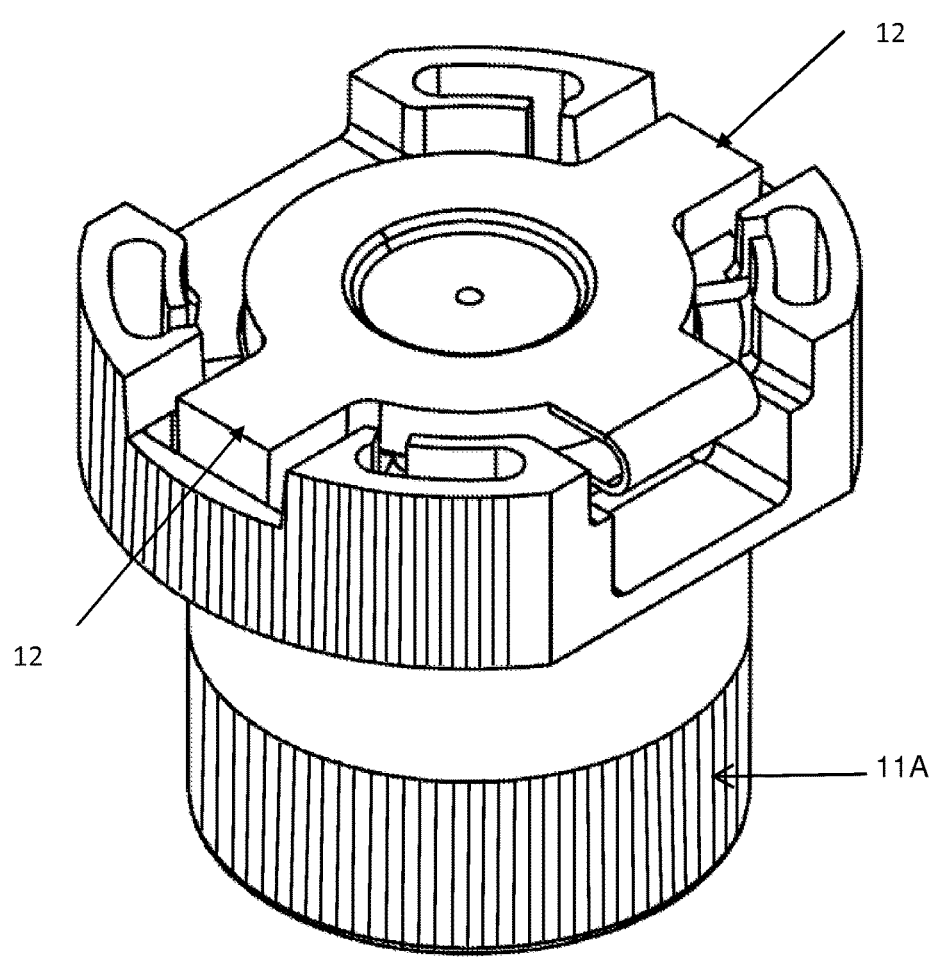

Shown in FIG. 7 is the integral cap sample cup with the alternative cap in the closed and locked position. Each locking tab (12) is shown mated to its corresponding slot (13). Also shown are the upwardly extending overflow chambers. Said overflow chambers extend vertically past the closed cap, providing increased surface area on the outside periphery of the upper body (2) to aid in gripping and manipulation of the sample cup. Further gripping means are indicated on the lower portion of outer member (11) in the area designated (11A) and along the outside periphery of the upper body (2).

Figure 8:
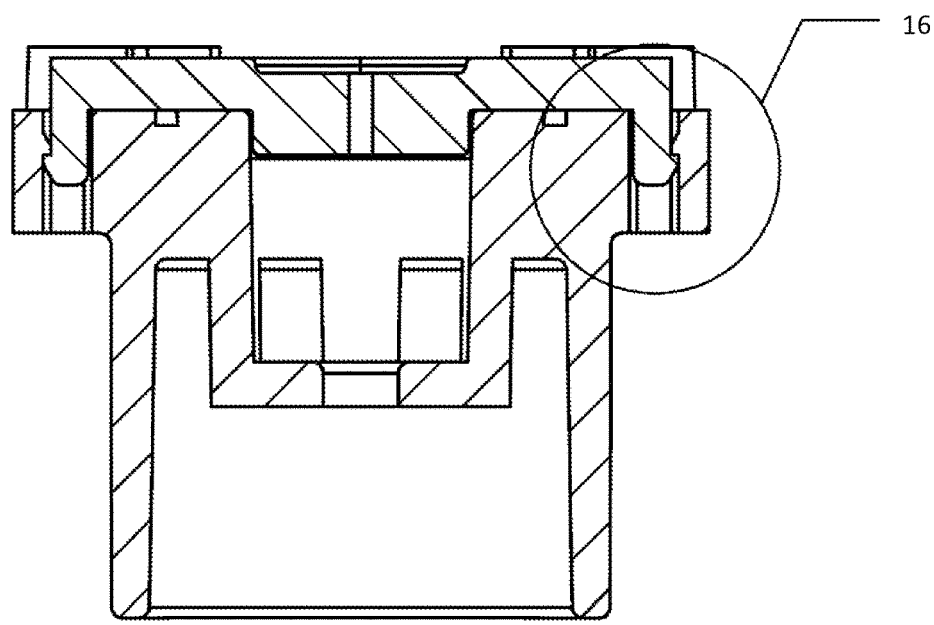

Shown in FIG. 8 is a side view of the integral cap sample cup with the alternative cap in the closed position. The callout (16) highlights one embodiment of the described mechanism securing the integral cap to the upper body of the sample cup.

Figure 9:
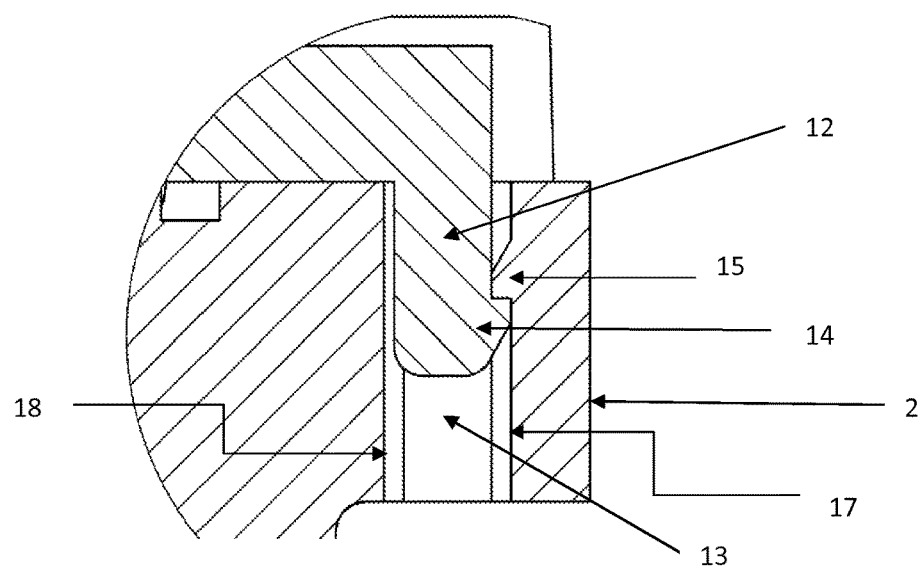

Shown in FIG. 9 is an enlarged view of the FIG. 8 callout. The hooked portion (14) of a locking tab (12) is shown mated to the hooked portion (15) of its corresponding slot (13), located on upper body (2). It is understood that the hooked portion (15) of a slot may be positioned along its outer wall (17) or inner wall (18) with the hooked portion (14) of a locking tab (12) being positioned to mate accordingly.

While the dimensions and shape of the sample cup components is not specifically defined and/or discussed herein, it is understood that such dimensions and shape may be adjusted or modified to meet industry needs or requirements without digressing from the spirit of the invention.

What is claimed:

1. A sample cup for retaining a sample to be analyzed spectrochemically, said sample cup comprising:
    a substantially cylindrical lower body with a bottom open end and integral upper body having a top open end and creating a flanged intersection with said lower body;
    an integral cap formed integral with said upper body and secured to said upper body by a hinge;
    an inner chamber suspended from said upper body into the interior of said lower body;
    said inner chamber comprising a cutout and a bottom stop;
    an outer member dimensioned to frictionally fit over said lower body;
    an overflow chamber positioned along the top of said upper body, wherein said overflow chamber is connected to the inner chamber via a first channel wherein the first channel is positioned at an upper surface of the upper body;
    and wherein a bottom surface of the overflow chamber is positioned at the first channel and the overflow chamber extends vertically to height greater than the upper surface of the upper body;
    and wherein the overflow chamber circumferentially surrounds a portion of the perimeter of the cap in the closed position and circumferentially surrounds a portion of the perimeter of the inner chamber when the cap is in the open position;
    and wherein each discrete overflow chamber extends radially from the inner chamber with each overflow chamber being positioned equidistant around the perimeter and connected to the inner chamber via the first channel;
    and wherein said overflow chamber is simultaneously open to the exterior when said integral cap is in a closed position, and wherein said overflow chamber is designed to contain any sample overflow within the exterior exposed portion of said upper body of the sample cup; and
    wherein a thin-film of material is secured across said bottom open end of said lower body by application of said outer member to contain a liquid sample for spectrochemical analysis.

2. The sample cup according to claim 1, wherein said upper body includes four discrete overflow chambers designed to contain any sample within the upper body of the sample cup.

3. The sample cup according to claim 1, wherein said overflow chamber extends vertically beyond said integral cap when said integral cap is in a closed position.

4. The sample cup according to claim 1, further comprising a vent hole in said integral cap.

5. The sample cup according to claim 1, further comprising an upper body dimensioned to contain said integral cap flush with the top edge of said upper body when said integral cap is in the closed position.

6. The sample cup according to claim 1, further comprising an upper body dimensioned to include parallel opposing flat surfaces disposed perpendicular to said top open end of said upper body.

7. The sample cup according to claim 1, wherein said outer member includes a gripping means situated on a lower portion of said outer member to facilitate handling of the assembled sample cup.

8. The sample cup according to claim 1, further comprising a first channel extending from the top outside edge of said inner chamber to said overflow chamber.

9. The sample cup according to claim 1, further comprising a second channel situated at least partially circumferentially about the upper body top open end.

10. The sample cup according to claim 1, further comprising a second channel situated at least partially circumferentially about the upper body top open end.

11. The sample cup according to claim 1, further comprising a gripping means on said upper body.

12. A sample cup for retaining a sample to be analyzed spectrochemically, said sample cup comprising:
    a substantially cylindrical lower body with a bottom open end and integral upper body having a top open end and creating a flanged intersection with said lower body;
    an integral cap formed integral with said upper body secured to said upper body by a hinge;
    said integral cap including two or more downward projecting locking tabs, each locking tab dimensioned to fit within a corresponding slot in said upper body;
    an inner chamber suspended from said upper body into the interior of said lower body;
    said inner chamber comprising a cutout and a bottom stop;
    an outer member dimensioned to frictionally fit over said lower body;
    an overflow chamber positioned along the top of said upper body, wherein said overflow chamber is connected to the inner chamber via a first channel wherein the first channel is positioned at an upper surface of the upper body;
    and wherein a bottom surface of the overflow chamber is positioned at the first channel and the overflow chamber extends vertically to height greater than the upper surface of the upper body;
    and wherein the overflow chamber circumferentially surrounds a portion of the perimeter of the cap in the closed position and circumferentially surrounds a portion of the perimeter of the inner chamber when the cap is in the open position;
    and wherein each discrete overflow chamber extends radially from the inner chamber with each overflow chamber being positioned equidistant around the perimeter and connected to the inner chamber via the first channel;
    and wherein said overflow chamber is simultaneously open to the exterior when said integral cap is in a closed position, and wherein said overflow chamber is designed to contain any sample overflow within the exterior exposed portion of said upper body of the sample cup; and wherein a thin-film of material is secured across said bottom open end of said lower body by application of said outer member to contain a liquid sample for spectrochemical analysis.

13. The sample cup according to claim 12, wherein said upper body includes four discrete overflow chambers designed to contain any sample within the upper body of the sample cup.

14. The sample cup according to claim 12, wherein said overflow chamber extends vertically beyond said integral cap when said integral cap is in a closed position.

15. The sample cup according to claim 12, further comprising a vent hole in said integral cap.

16. The sample cup according to claim 12, further comprising an upper body dimensioned to contain said integral cap flush with the top edge of said upper body when said integral cap is in the closed position.

17. The sample cup according to claim 12, further comprising an upper body dimensioned to include parallel opposing flat surfaces disposed perpendicular to said top open end of said upper body.

18. The sample cup according to claim 12, wherein said outer member includes a gripping means situated on a lower portion of said outer member to facilitate handling of the assembled sample cup.

19. The sample cup according to claim 12, further comprising a first channel extending from the top outside edge of said inner chamber to said overflow chamber.

20. The sample cup according to claim 12, further comprising a second channel situated at least partially circumferentially about the upper body top open end.

21. The sample cup according to claim 12, further comprising a second channel situated at least partially circumferentially about the upper body top open end.

22. The sample cup according to claim 12, further comprising a gripping means on said upper body.

* * * * *